US 6,749,867 B2
Jun. 15, 2004

(12) United States Patent
Robinson et al.

(54) DELIVERY SYSTEM FOR OMEPRAZOLE AND ITS SALTS (76) Inventors: Joseph R. Robinson, 41 Chequamegon Bay, Madison, WI (US) 53719; James W. McGinity, 4209 Dunning La., Austin, TX (US) 78746

( * ) Notice: Subject to any disclaimer, the term of this patent is extended or adjusted under 35 U.S.C. 154(b) by 40 days.

(21) Appl. No.: 09/991,059

(22) Filed: Nov. 21, 2001

(65) Prior Publication Data

US 2002/0160046 A1 Oct. 31, 2002

Related U.S. Application Data (60) Provisional application No. 60/253,828, filed on Nov. 29, 2000.

(51) Int. Cl.[7] .............................. A61K 9/14; A61K 9/48; A61K 9/20; A61K 9/16; A61K 9/22
(52) U.S. Cl. .................. 424/489; 424/464; 424/465; 424/468; 424/474; 424/490; 424/493; 424/451; 424/452; 424/475; 424/494; 424/495; 424/496; 424/491; 424/497; 424/498
(58) Field of Search ................. 424/464, 465, 424/468, 474, 489, 490, 493, 451, 452, 475, 495, 496, 494, 491, 497, 498

(56) References Cited

U.S. PATENT DOCUMENTS

| | | | |
|---|---|---|---|
| 4,786,505 A | * | 11/1988 | Lovgren et al. |
| 4,853,230 A | | 8/1989 | Lovgren et al. |
| 5,385,739 A | * | 1/1995 | Debregeas et al. |
| 5,470,584 A | | 11/1995 | Hendrickson et al. |
| 5,639,476 A | | 6/1997 | Oshlack et al. |
| 5,672,360 A | | 9/1997 | Sackler et al. |
| 5,783,212 A | | 7/1998 | Fassihi et al. |
| 6,077,541 A | | 6/2000 | Chen et al. |
| 6,149,942 A | | 11/2000 | Scheiwe et al. |
| 6,489,346 B1 | * | 12/2002 | Phillips |

FOREIGN PATENT DOCUMENTS

EP  0700285 B1  9/1998

OTHER PUBLICATIONS

Bodmeier, R. et al., The influence of Buffer Species and Strength on Diltiazem HC1 release from Beads Coated with the Aqueous Cationic Polymer Dispersions, Eudragit RS, RL 30D,Pharm. Res., 1996, vol. 13, No. 1: 52–56.

Bodmeier, R. et al., Polyactic acid microspheres containing quinidine base and quinidine sulphate prepared by the solvent evaporation method . . . ;J. Microencapsulation, 1988, vol. 5, No. 4: 325–330.

Maejima, T. et al., Influence of Film Additives on Stabilizing Drug Release Rates from Pellets Coated with Acrylic Polymers; AAPS PharmSci Supplement; Nov. 1999, vol. 1, No. 4: S–375.

(List continued on next page.)

Primary Examiner—Thurman K. Page
Assistant Examiner—Humera N. Sheikh
(74) Attorney, Agent, or Firm—Rick Matos; Innovar, L.L.C.

(57) ABSTRACT

The present invention provides a time-release dosage form for delivering an acid-labile pharmaceutical, such as omeprazole, into the upper portion of the gastrointestinal tract downstream of the stomach. The dosage form includes a drug-containing core surrounded by an inert time-release coating that delays release of the drug from the core until expiration of a certain time period after administration, generally 0.5–5.0 hours or 1–3 hours. When the gastrointestinal fluid contacts the core, the drug is released rapidly into the GI tract. The dosage form does not contain an enteric coating. The dosage form can also include one or more additional coatings exterior to the time-release coating to provide delivery of an immediately released loading dose of the acid-labile drug or another drug.

50 Claims, 3 Drawing Sheets

OTHER PUBLICATIONS

Lindberg, P. et al., Omeprazole: The First Proton Pump Inhibitor, Medicinal Research Reviews, 1990, vol. 10, No. 1: 1–54.

APHa Special Report, Gastroesophageal Reflux Disease: Simple Heartburn or Serious Disease?, APHa Special Report, 1999, 1–17.

Pilbrant, A. et al., Development of an Oral Formulation of Omeprazole, Scand. J. Gastroenterol, 1985, vol. 20 suppl. 108: 113–120.

Richards, J. P. et al., A relative bioavailability study of 2 oral formulations of omeprazole after their administration in repeated doses to healthy volumteers, Gastroenterol Hepatol, Apr.1999, vol. 22, No. 4: 171–175. Abstract.

Storpirtis, S. et al., In vitro evaluation of dissolution properties and degradation products of omeprazole in enteric--coated pellets, Drug Dev Ind Pharm, Nov. 1998, vol. 24, No. 11: 1101–1107. Abstract.

Hussain, F.N. et al., Mesalazine release from a pH dependent formulation: effects of omeprazole and lactulose co–administration, Br J Clin Pharmacol, Aug. 1998, vol. 46, No. 2: 173–175. Abstract.

Pillai, G. K. et al., Bioequivalence study of two capsule formulations of omeprazole, Acta Pharm Hung, Nov. 1996, vol. 66, No. 6: 231–235. Abstract.

Thomson, A.B., Pharmocokinetics and pharmacodynamics during treatment with the omeprazole 20 mg enteric–coated tablet and 20 mg capsule in asymptomatic duodenal ulcer patients, Can J Gastroenterol, Nov.–Dec. 1997, vol. 11, No. 8: 657–656. Abstract.

Pilbrant, A., Development of an oral formulation of omeprazole, Scand J. Gastroenterol Suppl, 1985, vol. 108: 113–120. Abstract.

Electronic Orange Book Online, Omeprazole.

* cited by examiner

DELIVERY SYSTEM FOR OMEPRAZOLE AND ITS SALTS

This application claims the benefit of No. 60/253,828 filed on Nov. 29, 2000.

FIELD OF THE INVENTION

The present invention relates to stabilized formulations of acid-labile drugs that provide a delayed and rapid release of the drug into the gastrointestinal tract. More particularly, the invention relates to an omeprazole formulation comprising a thick coating not containing a conventional enteric release polymer.

BACKGROUND OF THE INVENTION

Omeprazole is the first of a new class of drugs that inhibits gastric secretion by altering the activity of $H^+/K^+$ ATPase, the final common step of acid secretion in gastric parietal cells. Omeprazole is indicated as therapy for short-term treatment of active duodenal ulcers and is also used in the treatment of severe erosive esophagitis or poorly responsive symptomatic gastroesophageal reflux disease (GERD).

The plasma half-life of omeprazole is about 60 minutes; however, the duration of action of a single-dose may exceed 24 hours. The recommended dose of omeprazole is 20 mg daily for 4–8 weeks that may be repeated, if necessary.

Pilbrant and Cederberg (1985) reported on the physical and chemical properties of omeprazole. The drug has low water solubility and is chemically unstable in an acidic environment. Omeprazole degrades very rapidly in acidic aqueous solutions, and the rate of degradation proceeds with a half-life of less than 10 minutes, at pH values below 4. Although it is very slightly soluble in water, the drug is very soluble in alkaline solution as the negatively charged ion. At pH 6.5, the half-life of degradation was reported to be about 18 hours, and at pH 11, the half-life extends to several hundred days. Preformulation studies indicated that moisture, solvents, and acidic substances had a deleterious effect on the stability of omeprazole.

The resting pH of the stomach is generally less than 2 and a meal may increase the pH to between 3 and 5. The major physiological stimulus for acid secretion in the stomach is the ingestion of food, especially if the meal has a high protein content. It is the protein component of the meal that possesses the greatest buffering capacity. Foods, such as milk, can raise the gastric pH to values as high as 6. Gastric emptying times can show considerable variation between subjects according to the test methods used, and can generally vary between 0.5–2.0 hours.

To protect omeprazole from the hostile environment of the stomach, Pilbrant and Cederberg, and others, have applied an enteric coat to solid substrates, such as granules, containing omeprazole prior to conducting bioavailability studies in humans. A fully bioavailable dosage form for omeprazole must release the active drug rapidly in the proximal part of the gastrointestinal tract.

In U.S. Pat. No. 4,786,505, Lovgren et al disclose a pharmaceutical preparation containing omeprazole and salts together with other alkaline compounds. A core containing omeprazole is surrounded by an enteric release coating. A subcoating, that is water soluble or rapidly disintegrating in water, separates the core from the enteric coat that protects the preparation from the hostile environment of the stomach. Enteric coatings are also disclosed in U.S. Pat. No. 5,385,739. The subcoat or separating layer in the '505 patent and in U.S. Pat. No. 4,853,230, also serves to separate the omeprazole from the acidic pH environment of the enteric polymers, i.e., enteric polymers are generally applied as a solution to a core containing a drug. Such enteric polymers are generally acidic, and therefore are capable of degrading omeprazole in the core during application of the coating to the core. Conventional enteric polymers may include shellac, Eudragit™ L100 and S100, Eudragit™ L30D 55 and Eudragit FS30D, cellulose acetate phthalate, PVAP, HPMCAS and HPMCP, or similar materials that are insoluble in acidic environments or water and pass into solution at pH values above pH 5.0, the pH of the upper GI tract downstream from the stomach. Each of these references discloses that a separating layer must be used between the enteric coat and the core and that an enteric coat must be used in order to provide a suitable release profile. However, given the tendency of enteric release polymers to degrade omeprazole, a subcoating is required. The requirement for a subcoating unnecessarily complicates manufacture of a stabilized dosage form. The subcoating in these formulations does not delay release of the omeprazole from the core to any significant extent.

None of the known omeprazole formulations have employed non-enteric coatings, i.e., coatings that do not rely upon pH changes that occur in the GI tract, to effect a delayed and subsequently rapid release of omeprazole. Use of only a non-acidic non-enteric coating to effect the delayed and rapid release of omeprazole would be beneficial as it would simplify the method for manufacturing a stabilized dosage form.

SUMMARY OF THE INVENTION

The present invention seeks to overcome at least some of the above-mentioned disadvantages inherent in known omeprazole-containing formulations. Stable and bioavailable omeprazole solid dosage forms are disclosed herein. Accordingly, one aspect of the invention provides a stabilized formulation containing omeprazole, or a salt thereof, wherein the formulation does not require a separating layer or an enteric release coating. The present formulation provides a physically and chemically stable delivery system for omeprazole and its salts, maintains drug stability during storage, stabilizes omeprazole in the acidic portions of the GI tract of a patient, and provides a rapid release of omeprazole in the upper GI tract. The formulation of the invention does not require or include an enteric coating or a separating layer to protect the omeprazole in the core of the tablet.

The present omeprazole formulation can exist as any multiparticulate form such as granules, spheroids, microspheres, seeds, pellets, beads, microcapsules, agglomerates, mini-tablets or tablets that are manufactured employing conventional techniques and pharmaceutical excipients. The formulation optionally contains an alkalizing agent present in the core of the dosage form and/or in the non-enteric coating surrounding the core.

Instead of an enteric coating, the formulation of the invention includes a non-enteric time-release (TR) coating applied directly over the omeprazole-containing core. This coating can be applied using conventional or perforated coating pans, fluidized bed equipment or by compression coating. The composition of this coating is designed such that the core of the dosage form will rapidly (immediately or catastrophically) disintegrate into an aqueous environment of use when non-acidic media or digestive juice in the environment come into contact with the core. The TR coating generally possesses erosion and/or diffusion properties that are essentially independent of the pH of the external aqueous medium and of the enzymes and bile salts present in the GI tract.

One embodiment of the invention provides a solid dosage form for providing a delayed and subsequently rapid release of omeprazole into an environment of use, wherein the dosage form comprises:
- a core comprising omeprazole and at least one pharmaceutical excipient, wherein the core rapidly releases the omeprazole after the core is contacted with an aqueous fluid in an environment of use; and
- a non-enteric water soluble time-release coating surrounding and in contact with the core, wherein the coating delays the contact of the core with the aqueous fluid in the environment of use for a sufficient period of time to delay the release of the omeprazole from the core, and the coating subsequently loses its physical integrity after the delay period thereby permitting the core to rapidly release the omeprazole into the environment of use.

Specific embodiments of the invention include those wherein: 1) the dosage form includes plural coated cores which are granules, beads, pellets, spheroids, microspheres, or seeds that are compressed into a tablet or filled into a capsule; 2) the core contains one or more osmotic agents that promote a buildup of osmotic pressure in the core and aid in disintegrating the core following contact with an aqueous fluid; 3) the osmotic agents are alkaline reacting compounds or additional pharmaceutical excipients known in the art for use in preparing cores of solid dosage forms; 4) a disintegrant is present in the core to ensure that the core disintegrates in aqueous media; 5) the time-release coating comprises one or more hydrophilic or hydrophobic polymers optionally containing one or more additives that regulate the strength of the film, as well as the erosion and/or diffusion properties of the film; 6) the dosage form is adapted for oral administration, the time-release coating is sufficiently thick to retain its chemical and physical integrity in the stomach, and the time-release coating loses its physical integrity in the upper portion of the GI tract downstream from the stomach; 7) the time-release coating comprises one or more electrolytes, clays, polysaccharides and/or other hydrophilic materials to influence the period of time that it takes for the external aqueous medium to reach the core containing the drug; 8) the time-release coating begins to erode shortly after administration to a patient and continues to erode for a period of at least 1 hour after which it loses its physical integrity and exposes the core to the environment of use thereby providing a delayed release of omeprazole; 9) the time-release coating does not erode to a major extent but permits the diffusion of an aqueous fluid therein and delays exposure of the core to the aqueous fluid for a period of at least 1 hour after which time the core rapidly disintegrates and the time-release coating loses its physical integrity; 10) the time-release coating is about 100–5000, or 250–1000 at least about 100, microns thick and delays the release of omeprazole from the core at least about 1 hour after administration; 11) the time-release coating delays the release of omeprazole from the core 1–3 hours after administration; 12) the time-release coating also contains one or more buffering agents and/or alkalizing agents; 13) the time-release coating also contains one or more erosion regulators and/or diffusion regulators; 14) the time-release coating is applied onto the core as a solution or suspension; and/or 15) the time-release coating is compressed onto the core.

Another aspect of the invention provides a method of administering omeprazole orally comprising the step of:
- administering an oral solid pharmaceutical formulation consisting essentially of an omeprazole-containing core and a non-enteric time-release coating surrounding and in contact with the core, wherein the time-release coating delays release of the omeprazole for a period of about 0.5–5.0 hours after administration, after which the omeprazole is released rapidly from the core.

Specific embodiments of the invention also include those wherein: 1) the time-release coating delays the release of omeprazole from the core until expiration of about 1–3 hours after administration; 2) the omeprazole is released from the core over a period of about 0.1–120 minutes, or no more than 150 minutes, once the core is contacted with an aqueous fluid; 3) the core comprises a mixture of omeprazole and at least one pharmaceutical excipient; 4) the core comprises an inert substrate onto which is applied, by spraying or compression, a mixture comprising omeprazole and at least one pharmaceutical excipient; 5) the time-release coating delays the release of omeprazole in an approximately pH independent manner; 6) the dosage form provides an omeprazole duration of action of at least about 12 hours and is administered once or twice daily; 7) the dosage form provides an omeprazole duration of action of about 24 hours and is administered once daily; 8) the dosage form is used to treat GERD; 9) the dosage form is administered between meals; 10) the dosage form is administered during meals; 11) the dosage form is administered just prior to or just after a meal; 12) the time-release coating delays contact of the core with an aqueous fluid in the environment of use; 13) the time-release coating erodes after administration; 14) the time-release coating permits diffusion of an aqueous fluid therein after administration; and/or 15) the time-release coating comprises two or more adjacent layers of the composition comprising the time-release coating.

These and other aspects of this invention will be apparent upon reference to the following detailed description and attached figures. To that end, certain patents and other documents are cited herein to more specifically set forth various aspects of this invention. Each of these documents is hereby incorporated by reference in its entirety.

BRIEF DESCRIPTION OF THE FIGURES

The following figures form part of the present description and describe exemplary embodiments of the claimed invention, the full scope of which should not be unduly narrowed by these figures.

FIG. 2 depicts sectional side elevation views of another embodiment of a solid dosage form according to the invention. This figure depicts some of the various different stages of erosion of the time-release coating. After a major portion of the time-release coating has eroded, the core is exposed to the aqueous fluid environment of use. The coating slowly erodes in the gastrointestinal tract and when the solvent front reaches the drug-containing core, the tablet disintegrates to release the drug into solution.

DETAILED DESCRIPTION OF THE INVENTION

The present omeprazole-containing formulation provides a delayed and rapid release of omeprazole. Generally, the formulation is a solid-dosage form consisting of a core surrounded by a time-release coating. The present dosage form does not include what is conventionally referred to as an enteric release coating made from an enteric release polymer, neither does the dosage form include a "separating layer" between the core and the time-release coating. The core comprises omeprazole (or a pharmaceutically acceptable salt thereof) and at least one pharmaceutically acceptable excipient. The core provides a rapid release of omeprazole into an environment of use after the core has been exposed to an aqueous fluid in the environment of use. The time-release coating delays exposure of the core to the aqueous fluid thereby delaying the rapid release of omeprazole from the dosage form. The time-release coating has a predetermined thickness, or weight as compared to the core, and comprises a generally inert water soluble material that erodes in the environment of use and/or permits diffusion of an aqueous fluid therein (from the environment of use). In a first embodiment of the solid dosage form, omeprazole is rapidly released from the core after at least a major portion or all of the time-release coating has eroded thereby exposing the core to the aqueous fluid in the environment of use. In a second embodiment, omeprazole is rapidly released from the core after the aqueous fluid in the environment of use has diffused through the time-release coating to the core without the time-release coating having undergone a major amount of erosion. In a third embodiment, the time-release coating undergoes erosion and also permits diffusion of an aqueous fluid therein.

The dissolution, i.e. release, of acid-labile drug, such as omeprazole, from the pharmaceutical preparations of this invention is delayed by the presence of an external film coating that delays the disintegration of the drug-containing core and the resulting dissolution of the drug (less than 10% released) for a period of 0.5–5.0 hours, 1–3 hours, 1.5–2.5 hours, or 1.75–2.25 hours, after administration. After this time period, the acid-labile drug is released rapidly into the environment of use.

Omeprazole and its pharmaceutically acceptable salts are commercially available from a Astra-Zeneca™ (UK and Sweden) and sold under the trademarks PRILOSEC™ and LOSEC™. When referred to herein, omeprazole should be considered as being present in its salt-free form, in a salt form, or in a form that is a combination of the salt-free form and the salt form. All forms of omeprazole can be used in the invention and include, for example, isomeric, diastereomeric, enantiomeric, prodrug, regioisomeric, polymorph and derivative forms. Depending upon the material(s) employed for the time-release coating, the salt or salt-free form may be preferred.

The core of the solid dosage form is a substrate such as a granule, bead, pellet, mini-pellet, tablet core, particulate, capsule, spheroid, microsphere, microcapsule, mini-tablet or agglomerate. When present as a coated bead, granule, particulate or mini-pellet, plural coated beads, granules, particulates or mini-pellets can be compressed into a larger solid mass, or they can be enclosed in a capsule that releases the plural coated beads, granules, particulates or mini-pellets into the stomach shortly after administration. The core will comprise a mixture of the drug and at least one pharmaceutical excipient. Alternatively, the core will comprise an inert substrate onto which is applied the drug and at least one pharmaceutical excipient. A capsule (hard or soft) can also serve as the core, which is then coated with the TR coating.

Pellets can be formed as described herein or by preparing a drug containing dispersion in water or in a suitable solvent that is then sprayed or layered onto placebo cores (nonpareils). Drug-containing pellets can also be prepared using a rotor granulator or other suitable methods that are known in the art.

Examples 7 and 8 detail two specific methods for preparing the core; however, the core can be made by any method known for making pharmaceutically acceptable solid dosage forms. Such methods generally include traditional wet granulation, cold mass extrusion, or dry granulation techniques. The drug may be incorporated into the core using traditional tableting techniques. Alternatively, the drug may be applied to a placebo tablet by layering the drug in a suitable film coating formulation, before the time-release coating is applied. For example, the drug may be layered onto nonpareils or similar placebo delivery forms, prior to the addition of the TR coating.

Disintegration of the core granules or tablets will be approximately independent of the pH of the external release media.

The core containing omeprazole or omeprazole salt is formulated into an immediate-release formulation comprising at least one conventional pharmaceutical excipient which may include an alkalizing agent, antioxidant, buffering agent, disintegrant, binder, lubricant, preservative, adsorbent, antiadherent, diluent, direct compression excipient, glidant, opaquant, polishing agent or combination thereof.

After the core is formed, it is surrounded by a time-release coating. As used herein, the term "time-release coating" refers to a coating that delays the release of omeprazole from the present dosage form in a manner that is generally independent of the pH of an aqueous fluid to which the time-release coating is exposed in an environment of use. The time-release coating is unlike a conventional enteric coating, which provides a delayed release of a drug from an underlying core in a pH dependent manner. A time-release coating behaves differently than and comprises different components than an enteric coating. After a delay period, the time-release coating loses its physical integrity and permits release of omeprazole from the core of the solid dosage form. Exemplary formulations for and methods of making the time-release coating are detailed in Examples 1–6.

The time-release coating will generally comprise filmforming compounds such as cellulosic derivatives, such as hydroxypropylcellulose, methylcellulose, hydroxypropyl methylcellulose, hydroxyethylcellulose, and/or acrylic polymers including the non-enteric forms of the Eudragit™ brand polymers. Other film-forming materials may be used alone or in combination with each other or with the ones listed above. These other film forming materials generally include poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

A water soluble time-release coating will generally comprise an inert and non-toxic material that is at least partially, and generally substantially completely erodible in an environment of use. Selection of materials suitable for the time-release coating will depend upon the desired delay period for release of acid-labile drug from the core. Exemplary materials are disclosed in U.S. Pat. No. 4,576,604 to Guittard et al. and U.S. Pat. No. 4,673,405 to Guittard et al., and U.S. Pat. No. 6,004,582 to Faour et al. and the text *Pharmaceutical Dosage Forms: Tablets Volume I, 2nd Edition*. (A. Lieberman. ed. 1989, Marcel Dekker, Inc.), the relevant disclosures of which are hereby incorporated by reference.

Materials which are suitable for making the time-release coating of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer.

Other materials which can be used in the time-release coating include hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, and calcium pectinate can be included in the time-release coat.

The time-release coating can further comprise hydrophilic and/or hydrophobic polymers or film forming compounds that optionally contain further additives that help to control the erosion of the film coating in aqueous media and/or control the permeation of aqueous media through the film coat to the core of the preparation containing the active drug substance. The time-release coating can comprise one or more "erosion regulators" and/or "diffusion regulators". An individual material or combination of materials may serve as an erosion regulator and/or a diffusion regulator. The TR coating can also comprise a sweetening agent, colorant or flavorant.

As used herein, an erosion regulator is a material or combination of materials that controls the erosion of the time-release coating in an aqueous fluid. Exemplary erosion regulators include hydrophilic polymers, electrolytes, proteins, peptides, amino acids and others known to those of ordinary skill in the pharmaceutical sciences.

As used herein, a diffusion regulator is a material or combination of materials that controls the diffusion of an aqueous fluid through the time-release coating. Exemplary erosion regulators include hydrophilic polymers, electrolytes, proteins, peptides, amino acids and others known to those of ordinary skill in the pharmaceutical sciences.

The actual character of the coat, e.g., erodible coat or water diffusible coat, used in the dosage form will depend upon the erosion regulator and/or diffusion regulator and the time-release material included in the coat.

The TR omeprazole systems will be designed such that the disintegration of the drug containing solid substrate is controlled by either the diffusion of moisture through the film coat or alternatively controlled by the erosion of the external coating. Drug release may also be controlled by a combination of these two mechanisms. The addition of hydrophilic polymers, electrolytes, clays, polysaccharides and other hydrophilic materials in the film coating will influence the time period for the external aqueous medium to reach the pellet or tablet core containing the drug.

Figure 1:
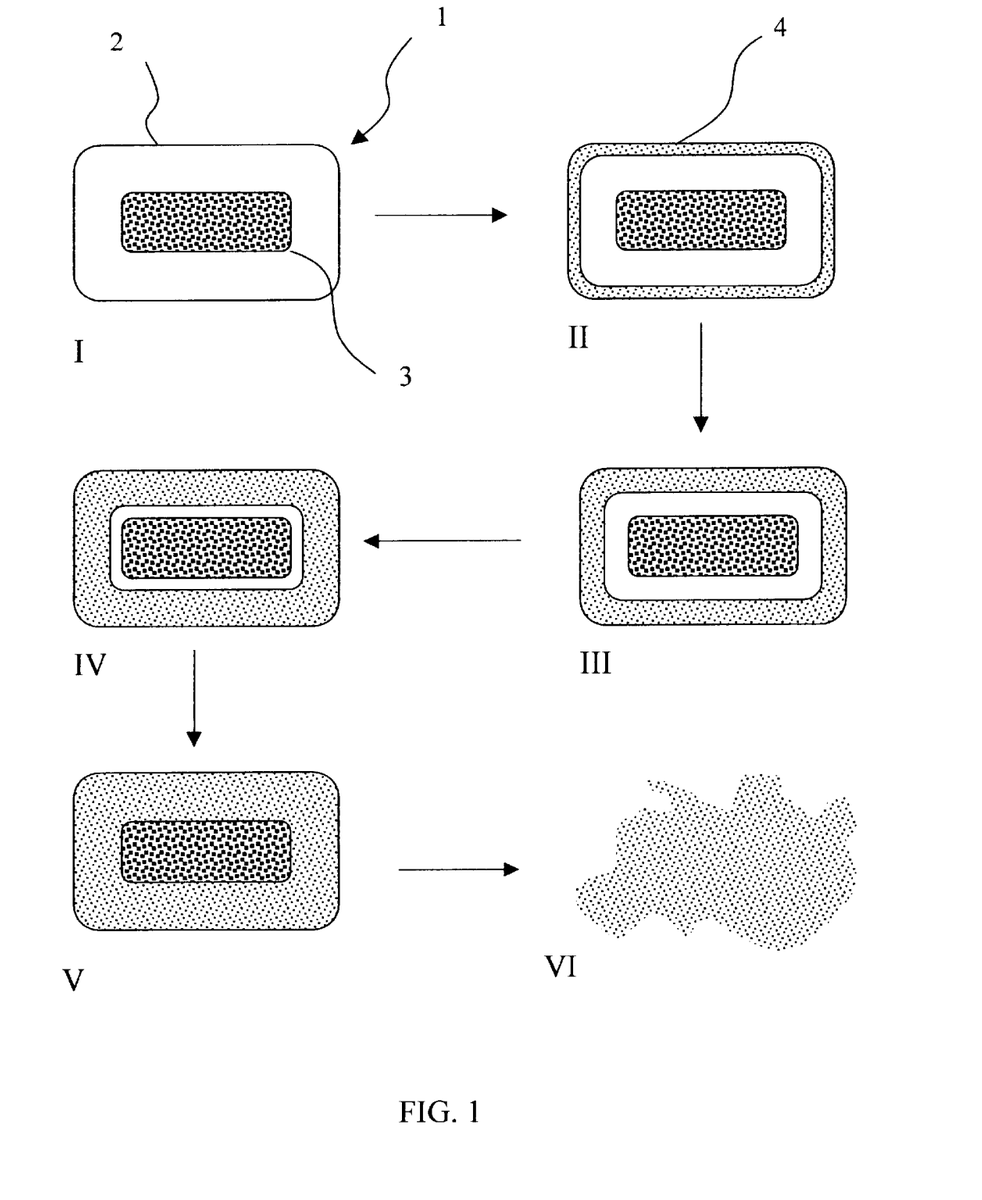
FIG. 1 depicts sectional side elevation views of a solid dosage form according to the invention consisting essentially of a tablet core comprising omeprazole, or an alkaline salt of omeprazole, and a time-release coating. This figure depicts some of the various different stages of diffusion of water into the time-release coating. The release media diffuses through the coating and when the solvent front reaches the drug-containing core, the tablet disintegrates and the drug passes into solution.
Figure 2:
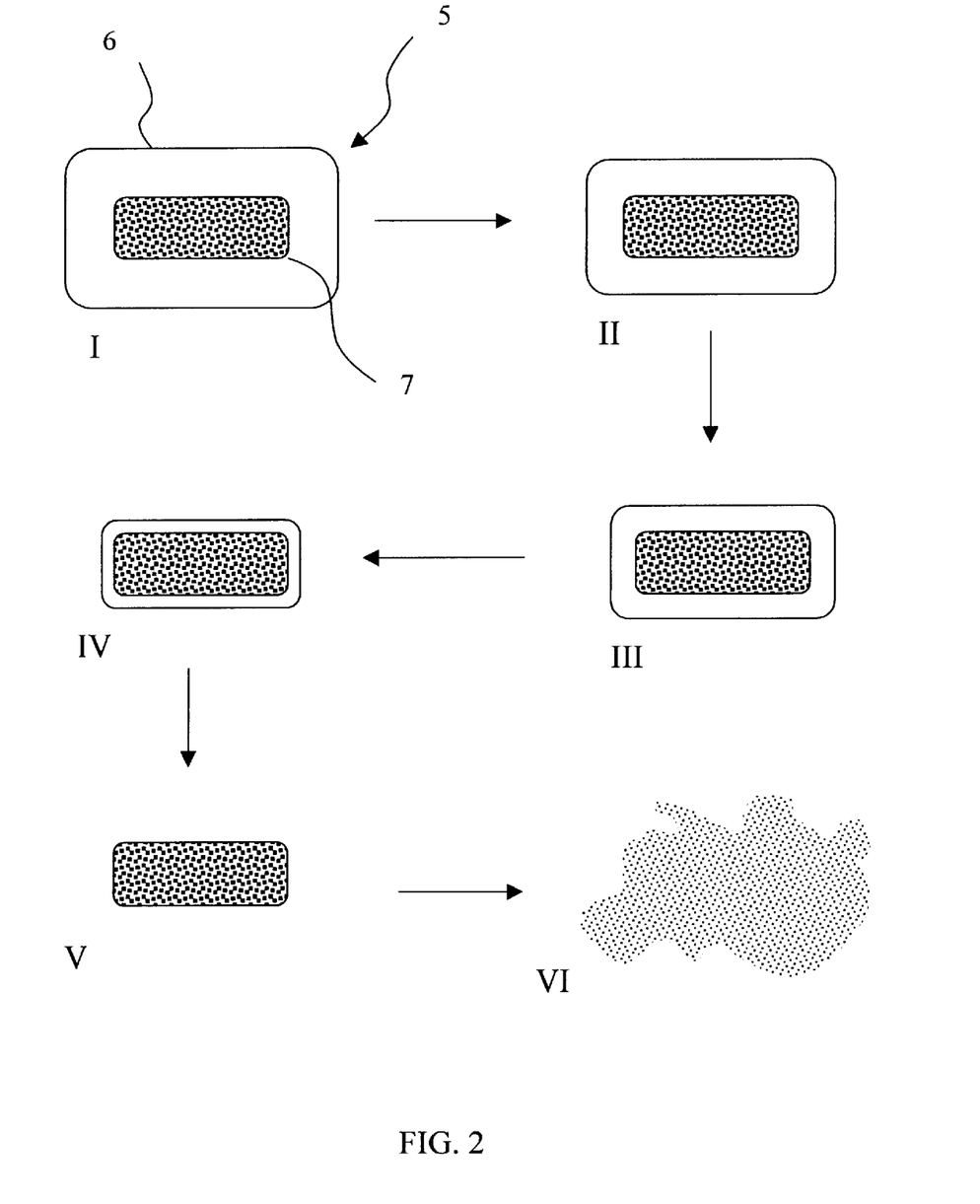

Exemplary schematics for the diffusion-controlled and erosion-controlled systems are depicted in FIGS. 1 and 2, respectively. Both mechanisms will generally occur to some degree in each model, however, the selection of ingredients for the TR coating layer will ensure that one or the other mechanism will predominate.

For example, a coating the controls the diffusion of water therein and does not significantly erode over time gradually is depicted in FIG. 1. In this exemplary system, the time-release coating (2) of the dosage form (1) begins to permit diffusion of an aqueous solution therein shortly after administration forming a partly hydrated coating (4) surrounding the TR coating and the core (3). As the time after administration increases the extent to which the aqueous fluid has diffused into the coating increases as exemplified by Stages I to IV. Gradually, the aqueous fluid diffuses completely through the time-release coating (Stage V) and contacts the core, at which time the core disintegrates and rapidly releases drug (Stage VI). An example of such coating is described in Example 4.

According to another example, a coating that predominantly erodes over time gradually is depicted in FIG. 2. In this system, the dosage form (5) comprises time-release coating (6) surrounding the core (7) (Stage I). The TR coating begins to erode shortly after administration in an aqueous fluid and proceeds to undergo various different stages of erosion (Stages II–IV). After expiration of a lag time, the coating has eroded completely, or to a major extent, (Stage V) and the aqueous fluid contacts the core, at which time the core disintegrates and rapidly releases drug (Stage VI). An example of such coating is described in Example 6.

The quantity of time-release coating needed for each formulation will depend upon the surface area of the core, or the particle size of the pellets/granules, in order to control the lag time for drug released from the core.

Figure 3:
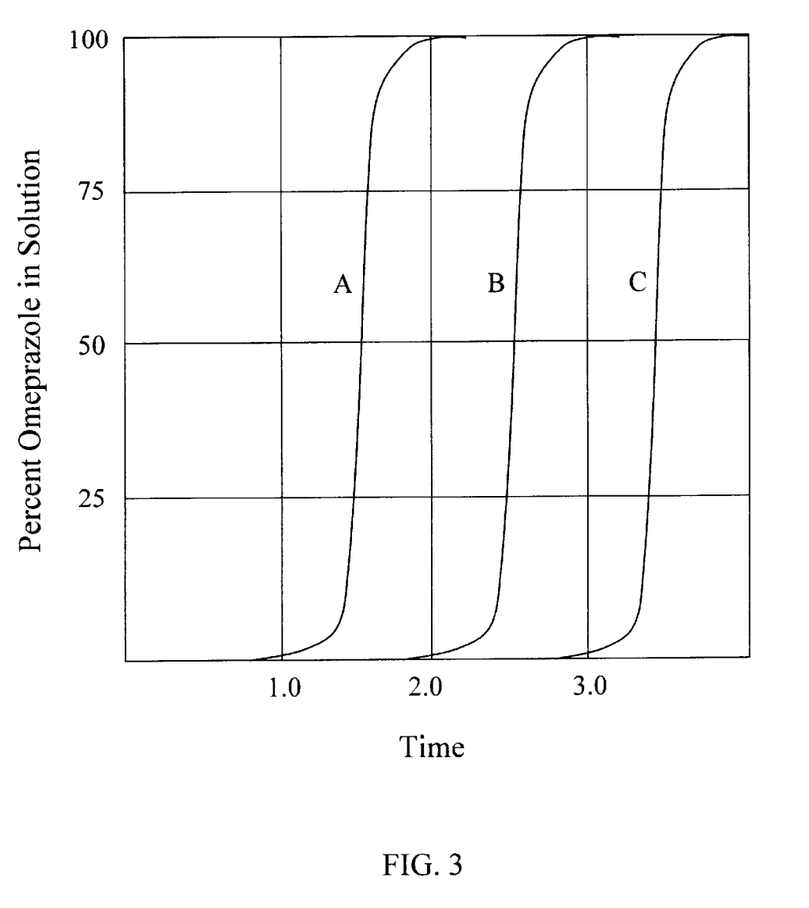
FIG. 3 depicts a graph demonstrating an exemplary relationship between the thickness of the time-release coating on the release of omeprazole from a time-release pellet or tablet. As the thickness of the coating layer increases from A to C, the lag time, i.e., the delay in the period of time it takes to begin releasing omeprazole from the core, increases.

The thickness of the time-release coating will control the time required for an aqueous solution to penetrate or erode the coating and reach the core. The influence of film thickness on the lag time for the core tablet to disintegrate and release drug is depicted in FIG. 3. As additional coatings of the same composition are applied to tablet cores, the thickness of the time-release coating increases, and the time (lag time) to disintegrate the tablet and to release the drug into solution increases, as shown by Profiles "A–C". Generally, the time-release coating will be about 100–5000 microns, or about 250–1000 microns, or at least about 200 microns thick, depending upon the material(s) from which it is made. For example, an erodible time-release coating that provides a lag time of about 0.5–2.5 hours will generally be about 100–2000 microns thick, and one that provides a lag time of about 2.5–5.0 hours will generally be about 2000–5000 microns thick. Similarly, a diffusion controlling time release coating that provides a lag time of about 0.5–2.5 hours will generally be about 200–1000 microns thick, and one that provides a lag time of about 2.5–5.0 hours will generally be about 1000–3000 microns thick.

The dissolution/release profiles depicted in FIG. 3 are sigmoidal and generally indicate that a small portion of the drug in the core may be released prematurely, i.e., before the TR coating has lost its physical integrity. Generally, the amount of drug that is released, i.e., that leaches from the core, prematurely is generally less than 10% wt. of the total drug load present in the core.

Once the TR coating has lost its physical integrity, the major portion of the drug in the core will be released rapidly over a period of 0.5 min to 1.5 hours, 0.5 min to 1.0 hour, or 0.1 to 120 min.

Depending upon the substrate being coated, the weight gain for the coated pharmaceutical dosage forms will generally be from about 25–400% in order to maintain the cores in a dry state during the first 1–3 hours of the dissolution process. Weight gains of 75–150% are more preferred. For more hydrophobic coatings, the thickness of the coating would be significantly less than for hydrophilic coatings that would slowly hydrate and erode from either the surface of the film coated tablet, or the coated pellet.

Since the coatings and additives are non-enteric in nature, drug release from these pharmaceutical preparations would be minimally influenced by the pH of the external milieu. The pH of the film coating during application onto the core is generally maintained in the neutral to alkaline range, or in the pH range of about 8–10. This pH range may be achieved by the incorporation of suitable buffering agents or inherently alkaline additives, such as bentonite, Veegum®, magnesium stearate or similar alkaline materials, into the composition from which the time-release coating is made. The presence of slightly acidic additives in the film coat will generally require the inclusion of buffer agents or alkaline components to ensure a pH above about 5 or 6.

Additives added to the film coating formulation to regulate erosion or the rate of penetration of moisture into the drug-containing core may include talc, bentonite, Veegum®, hectorite, and other insoluble clays and silicates, among others. Ethylcellulose, waxes and lipids, in addition to the mono-, di-and tri-glycerides are also suitable. For hydrophobic and water insoluble coatings, the permeability of the coatings may be regulated with water soluble agents such as the hydrophilic polymers, polysaccharides, electrolytes, buffers and materials of the like that would promote the hydration and swelling of the polymer, as well as the penetration of the aqueous medium through the membrane and into the drug-containing core. The presence of alkaline materials in the coating will also ensure that the fluid reaching the drug-containing cores will have a pH greater than 7.0 and will not degrade the acid-labile drug, such as omeprazole or salts of omeprazole, on contact.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, organic amine base, alkaline amino acids and trolamine and others known to those of ordinary skill in the art.

Suitable binders are generally non-acidic binders. Suitable hydrophobic binders include poly(vinyl acetate), polyethylene cellulose propionate high molecular weight (200,000), cellulose propionate medium molecular weight (75,000), cellulose propionate low molecular weight (25,000), cellulose acetate, cellulose nitrate, ethylcellulose, polyvinyl acetate, and non-enteric acrylic polymers, including EUDRAGIT™ RS, RL, NE 30D, and E100. Suitable hydrophilic binders also include poly(vinylpyrrolidone) high molecular weight (360,000), poly(vinylpyrrolidone) medium molecular weights (24,000 and 40,000), poly(vinylpyrrolidone) low molecular weight (10,000), vinyl alcohol polymer, poly(ethylene oxide), water soluble or water swellable cellulosic and starch derivatives, others known to those of ordinary skill in the art and mixtures thereof. Other binders include, by way of example and without limitation, acacia, carboxymethylcellulose sodium, compressible sugar (e.g., NuTab™), ethylcellulose, gelatin, liquid glucose, methylcellulose, povidone, gelatin and pregelatinized starch and others known to those of ordinary skill in the art. Examples of other binders which can be added to the formulation include, for example, tragacanth, starch, polyethylene glycol, guar gum, polysaccharides, sugars, polyols, xylitol, sorbital, invert sugars, poloxomers (PLURONIC™ F68, PLURONIC™ F127), collagen, albumin, gelatin, polyols (including xylitol), cellulosics, other known to those of ordinary skill in the art and combinations thereof. Other binders also include, for example, polypropylene glycol, polyoxyethylene-polypropylene copolymer, polyethylene ester, polyethylene sorbitan ester, poly(ethylene oxide) or combinations thereof and others known to those of ordinary skill in the art.

As used herein, the term "antioxidant" is intended to mean an agent that inhibits oxidation and thus is used to prevent the deterioration of preparations by oxidation. Such compounds include, by way of example and without limitation, ascorbyl palmitate, butylated hydroxyanisole, butylated hydroxytoluene, monothioglycerol, sodium ascorbate, sodium formaldehyde sulfoxylate and sodium metabisulfite and others known to those of ordinary skill in the art. Other suitable antioxidants include, for example, BHT, BHA, sodium bisulfite, vitamin E and its derivatives, propyl gallate or a sulfite derivative.

Buffering agents are used to control the pH of an aqueous solution in which the film is immersed so as to maintain the pH of the core in the approximately neutral or alkaline range. A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art.

Preservatives include compounds used to prevent the growth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "sweetening agent" is intended to mean a compound used to impart sweetness to a preparation. A sweetening agent may be included in the time-release coating or other exterior coating of the tablet. Such compounds include, by way of example and without limitation, aspartame, dextrose, glycerin, mannitol, saccharin sodium, sorbitol and sucrose and other materials known to one of ordinary skill in the art.

As used herein, the term "antiadherent" is intended to mean agents which prevent the sticking of solid formulation ingredients to punches and dies in a tableting machine, for example, during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "diluent" or "filler" is intended to mean inert substances used as fillers to create the desired bulk, flow properties, and compression characteristics in the preparation of the cores. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in direct compression formulations. Such compounds include, by way of example and without limitation, dibasic calcium phosphate (e.g., Ditab) and other materials known to one of ordinary skill in the art.

As used herein, the term "glidant" is intended to mean agents generally used in tablet or capsule formulations to reduce friction during tablet compression. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "lubricant" is intended to mean substances generally used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "opaquant" is intended to mean a compound used to render a coating opaque. May be used alone or in combination with a colorant. Such compounds include, by way of example and without limitation, titanium dioxide and other materials known to one of ordinary skill in the art.

As used herein, the term "polishing agent" is intended to mean a compound used to impart an attractive sheen to coated cores. Such compounds include, by way of example and without limitation, camauba wax, white wax and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel™), carboxymethylcellulose calcium, cellulose polyacrilin potassium (e.g., Amberlite™), alginates, sodium starch glycolate, gums such as agar, guar, locust bean, karaya, pectin, tragacanth and other materials known to one of ordinary skill in the art.

Exemplary osmagents or osmotic agents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

The dosage form of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethylene glycol) 450, with petroleum hydrocarbons, such as mineral oil and petrolatum; with water, or with mixtures thereof; with or without the addition of a pharmaceutically suitable surfactant, suspending agent or emulsifying agent.

Various other components, not otherwise listed above, can be added to the present formulation including, by way of example and without limitation, glyceryl monostearate, nylon, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly(vinyl chloride), 1,3-butyleneglycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

By the term "effective amount", it is understood that, with respect to, for example, pharmaceuticals, a therapeutically effective amount is contemplated. A therapeutically effective amount is the amount or quantity of acid-labile drug, such as omeprazole, which is sufficient to elicit the required or desired therapeutic response, or in other words, the amount that is sufficient to elicit an appreciable biological response when administered to a patient.

The solid dosage form of the invention can assume any shape or form known in the art of pharmaceutical sciences. The dosage form of the invention can be a pill, sphere, tablet, bar, plate, paraboloid of revolution, ellipsoid of revolution or the like. The dosage form can also include surface markings, cuttings, grooves, letters and/or numerals for the purposes of decoration, identification and/or other purposes.

The dosage form of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The rate at which gastric emptying occurs varies from person to person; however, the average adult will generally experience a gastric emptying within about 0.5–2.0 hours after eating or administration of a solid. Gastric emptying is generally faster when a solid dosage form is taken only with a liquid and absent any other solids. In this latter case, gastric emptying generally occurs within about 0.5–1.0 hours after administration of the dosage form.

Generally, the dosage form of the invention will release its charge of omeprazole in the upper GI tract downstream of the stomach. Since gastric emptying rates vary among people, the omeprazole may be released into the duodenum, jejunum, ileum, cecum, or small intestines.

The gastric emptying rate of small tablets and pellets is more uniform than the gastric emptying times of large tablets. The emptying of enteric coated pellets is dependent upon the nature of the capsule shell and how quickly the contents of the capsule disperses, since the volume of fluid available for dissolution is low in the stomach of a fasted individual. Tablets will empty more slowly in the presence of food, when they are dispersed in a large volume of food.

The dosage form of the invention is used to orally administer an acid-labile drug in a substantially or essentially or approximately pH independent manner such that release of the drug is delayed until after the dosage form passes the stomach. In one embodiment, the dosage form provides a therapeutic duration of action of at least about 12 hours can be administered once or twice daily. In another embodiment, the dosage form provides a therapeutic duration of action of about 24 hours and is administered once daily. When the drug is omeprazole, the dosage form can be used to treat GERD. Since drugs are metabolized, the dosage form of the present invention provides therapeutically effective blood plasma levels of any active metabolites of a drug administered in the dosage form. Accordingly, the invention also provides a method of maintaining therapeutically effective blood plasma levels of omeprazole and any active metabolite of omeprazole. The method comprises the step of administering an omeprazole-containing dosage form to a subject, wherein the dosage form provides a delayed release of omeprazole into the gastrointestinal tract of the subject downstream from the stomach in a pH independent manner by erosion or dissolution of a time-release coating surrounding an omeprazole-containing core followed by erosion or dissolution of the core or by diffusion of drug through a time-release coating surrounding an omeprazole-containing core followed by erosion or dissolution of the core. In an alternate embodiment, the core does not erode or dissolve but delivers drug by diffusion.

Depending upon the desired therapeutic action, patient response and other factors, the dosage form may be administered between meals, during meals, just prior to a meal or just after a meal.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

The following example details a method for the preparation of a solid dosage form having a time-release coating that undergoes erosion and also permits a controlled diffusion of water therein. The dosage form contains the following ingredients present in approximately the amounts indicated.

| Ingredient | Amount (% by wt.) |
|---|---|
| Aquacoat* | 10 |
| HPMC | 5 |
| talc | 18 |
| dibutyl sebacate | 2.5 |
| propylene glycol | 1.5 |
| water | q.s. 100 |

*Dry solid content

A dispersion containing the above-mentioned ingredients is agitated for 24 hours and then diluted with additional water as needed to provide the desired solids content. The resulting dispersion (or solution) is then sprayed onto the drug-containing solid composite, prepared according to Example 7 or 8, in either a fluidized bed unit (for pellets or granules) or in a coating pan (for tablets). The inlet temperature for the apparatus is approximately 65° C. and the outlet temperature is approximately 45° C. A spray rate of 2–10 g/min. may be employed for a Strea I (pellets) apparatus or Vector Hi-Coater (tablets) apparatus. The spray rate will depend upon batch size.

EXAMPLE 2

The following example details a method for the preparation of a solid dosage form having a time-release coating that predominantly permits a controlled diffusion of water through it and finally erodes. The dosage form contains the following ingredients present in approximately the amounts indicated.

| Ingredient | Amount (% by wt.) |
|---|---|
| Surelease* | 15 |
| HPMC | 2.0 |
| magnesium stearate | 0.25 |
| talc | 25 |
| glycerin | 0.5 |
| magnesium trialicate | 0.5 |
| disodium hydrogen phosphate | 0.5 |
| water | q.s. 100 |

*Dry solid content

A dispersion containing the above-mentioned ingredients is agitated for 24 hours and then diluted with additional water as needed to provide the desired solids content. The resulting dispersion (or solution) is then sprayed onto the drug-containing solid composite, prepared according to Example 7 or 8, in either a fluidized bed unit (for pellets or granules) or in a coating pan (for tablets). The inlet temperature is approximately 80° C. and the outlet temperature is 45° C. A spray rate of 2–20 g/min. for a fluidized bed coating unit or a perforated pan tablet-coating unit is employed. The solids content of the spray dispersion is 10–15% w/w. The spray rate will depend upon batch size.

EXAMPLE 3

The following example details a method for the preparation of a solid dosage form having a time-release coating that predominantly permits a controlled diffusion of water through it. The dosage form contains the following ingredients present in approximately the amounts indicated.

| Ingredient | Amount (% by wt.) |
| --- | --- |
| Eudragit ™ RS30D/RL30D (*2:1) | 15 |
| glycerol monostearate | 2 |
| talc | 10 |
| triethyl citrate | 0.5 |
| Veegum | 5 |
| dipotassium hydrogen phosphate | 0.5 |
| water | q.s. 100 |

*Dry solid content

A dispersion containing the above-mentioned ingredients is agitated for 24 hours and then diluted with additional water as needed to provide the desired solids content. The resulting dispersion (or solution) is then sprayed onto the drug-containing solid composite, containing the omeprazole or alkaline salt of omeprazole, in either a fluidized bed unit (for pellets or granules) or in a coating pan (for tablets). The inlet temperature is approximately 55° C. and the outlet temperature is 38° C. A spray rate of 2–10 g/min. for a fluidized bed coating unit or a perforated pan tablet-coating unit is employed.

EXAMPLE 4

The following example details a method for the preparation of a solid dosage form having a time-release coating that predominantly permits a controlled diffusion of water through it. The dosage form contains the following ingredients present in approximately the amounts indicated.

| Ingredient | Amount (% by wt.) |
| --- | --- |
| Eudragit ™ RS30D/RL30D (*4:1) | 18 |
| TEC | 4.0 |
| Lactose | 0.5 |
| Titanium dioxide | 15 |
| HPMC | 2 |
| Talc | 5 |
| Ethyl alcohol | 20 |
| magnesium stearate | 10 |
| water | q.s. 100 |

*Dry solid content

A dispersion containing the above-mentioned ingredients, except the alcohol, is agitated for 24 hours and then diluted with additional water as needed to provide the desired solids content. Alcohol is then added to the dispersion. The resulting dispersion (or solution) is then sprayed onto the drug-containing solid composite, containing the omeprazole or alkaline salt of omeprazole, in either a fluidized bed unit (for pellets or granules) or in a coating pan (for tablets). The inlet temperature is approximately 50° C. and the outlet temperature is 36° C. for both fluidized bed and pan coating equipment. A spray rate of 2–100 g/min. for a fluidized bed coating unit or a perforated pan tablet-coating unit is employed. The spray rate will vary depending on the batch size and the composites being coated.

EXAMPLE 5

The following example details a method for the preparation of a solid dosage form having a time-release coating that predominantly permits a controlled diffusion of water through it. The dosage form contains the following ingredients present in approximately the amounts indicated.

| Ingredient | Amount (% by wt.) |
| --- | --- |
| Aquacoat ™* | 16 |
| magnesium stearate | 10 |
| dibutyl sebacate | 4.2 |
| HPMC | 2.0 |
| titanium dioxide | 3 |
| glyceryl monostearate | 8 |
| lactose | 1 |
| water | q.s. to 100 |

*Dry solid content

A dispersion containing the above-mentioned ingredients is agitated for 24 hours and then diluted with additional water as needed to provide a solids content of about 12–15% w/w. The resulting dispersion (or solution) is then sprayed onto the drug-containing solid composite, containing the omeprazole or alkaline salt of omeprazole, in either a fluidized bed unit (for pellets or granules) or in a coating pan (for tablets). The inlet temperature is approximately 68° C. and the outlet temperature is 40° C. A spray rate of about 4 g/min. for a fluidized bed coating unit or a perforated pan tablet-coating unit is employed.

EXAMPLE 6

The following example details a method for the preparation of a solid dosage form having a time-release coating that predominantly erodes during use. The dosage form contains the following ingredients present in approximately the amounts indicated.

| Ingredient | Amount (% by wt.) |
| --- | --- |
| Eudragit ™ NE30D* | 15 |
| talc | 28 |
| magnesium stearate | 5 |
| glycerol monostearate | 5 |
| triethyl citrate | 0.5 |
| water | q.s. 100 |

*Dry solid content

A dispersion containing the above-mentioned ingredients is agitated for 24 hours and then diluted with additional water as needed to provide the desired solids content. The resulting dispersion (or solution) is then sprayed onto the drug-containing solid composite, containing the omeprazole or alkaline salt of omeprazole, in either a fluidized bed unit (for pellets or granules) or in a coating pan (for tablets). The inlet temperature is approximately 55° C. and the outlet temperature is 31° C. A spray rate of about 3 g/min. for a fluidized bed coating unit or a perforated pan tablet-coating unit is employed.

EXAMPLE 7

This example details a general method for the preparation of a tablet core that can be subsequently coated with a time-release coating as described herein.

| Ingredient | Amount (% by wt.) |
| --- | --- |
| Omeprazole | 22 |
| Silicified microcrystalline cellulose (SMCC) | 49 |

-continued

| Ingredient | Amount (% by wt.) |
| --- | --- |
| Dipotassium hydrogen phosphate | 1 |
| Fast Flow Lactose (FFL) | 18 |
| Ac-Di-Sol | 3 |
| Veegum | 3 |
| talc | 3 |
| Cab-O-Sil M5P | 0.5 |
| magnesium stearate | 0.5 |

The above ingredients are passed through a No. 60 mesh screen. Omeprazole, SMCC, FFL, Ac-Di-Sol, talc and Veegum were blended for 10 minutes. The Cab-O-Sil, magnesium stearate, and the dipotassium hydrogen phosphate are blended for 5 minutes to form an excipient composition. The omeprazole-containing powder mixture and excipient composition are mixed and blended for an additional 5 minutes to form the final pharmaceutical composition, which is compressed into tablets on a single punch or rotary tablet press.

EXAMPLE 8

This example details a general method for the preparation of pellets or granules that can be subsequently coated with a time-release coating as described herein.

| Ingredient | Amount (% by wt.) |
| --- | --- |
| Omeprazole | 28 |
| microcrystalline cellulose | 42 |
| PVP K30 | 3 |
| lactose | 20 |
| corn starch | 4 |
| Veegum ® | 1 |
| talc | 3 |
| disodium hydrogen phosphate | 2 |
| purified water | q.s. |

The omeprazole, MCC, lactose and corn starch are passed through a No. 60 mesh screen and blended for 10 minutes. The PVP, Veegum®. and disodium hydrogen phosphate are dispersed in the purified water and then added to the powder mixture to form a damp mass. This material is then processed in a marumerizer to form cylindrical extrudants that are then spheronized into pellets/blends, using cold mass extrusion.

EXAMPLE 9

The following example details a method for the preparation of a solid dosage form having a time-release coating that is compressed onto a core. In this embodiment, the time-release coating is compressed onto the tablet core. The dosage form contains the following ingredients present in approximately the amounts indicated. Drug release mechanisms for this example will primarily be erosion, however, some diffusion of water through the timed-release coating will also occur.

| Ingredient | Amount (% by wt.) |
| --- | --- |
| HPMC | 37 |
| Eudragit RS30D/RS30D | 20*<br>(4:1) |
| dibasic calcium phosphate | 25 |

-continued

| Ingredient | Amount (% by wt.) |
| --- | --- |
| talc | 14 |
| triethyl citrate | 3 |
| Cab-O-Sil M5P | 1 |
| purified water | q.s. |

*dry solids content

The granulation to be used for the compression coating is prepared by first adding the talc and the triethyl citrate to the acrylic dispersion. The suspension is then diluted with purified water and allowed at least one hour for the TEC to plasticize the Eudragit™ dispersion. The HPMC, dibasic calcium phosphate and the Cab-O-Sil M5P are then mixed to form a homogeneous blend. Granules are formed by the addition of the acrylic suspension to the powder blend in a fluidized bed unit, a high shear granulator or other similar granulating units that are known in the art.

The dried granules are then passed through a No. 20 mesh screen. Magnesium stearate (0.5%) is added to the granules that are then compressed onto the drug containing cores.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. A solid dosage form that provides a delayed and subsequently rapid release of omeprazole into an environment of use, wherein the dosage form comprises:
   a core comprising omeprazole and at least one pharmaceutical excipient, wherein the core rapidly releases the omeprazole after the core is contacted with a fluid in an environment of use; and
   a time-release non-enteric water soluble or water erodible coating surrounding and in contact with the core, wherein the coating delays the contact of the core with a fluid in an environment of use for a sufficient period of time to delay the release of the omeprazole from the core, and the coating loses its physical integrity in an essentially pH independent manner after the delay thereby permitting the core to rapidly release the omeprazole into the environment of use; and
   wherein, the dosage form excludes an enteric release coating made from an enteric release polymer; the dosage form is adapted for oral administration; the time-release coating is sufficiently thick to retain its chemical and physical integrity in the stomach when administered orally; and the time-release coating loses its physical integrity in the upper portion of the GI tract downstream from the stomach thereby releasing omeprazole.

2. The solid dosage form of claim 1, wherein the dosage form is a granule, bead, pellet, tablet, agglomerate, crystal, spheroid, microsphere, seed, capsule, microcapsule, or mini-tablet.

3. The solid dosage form of claim 2 wherein, the dosage form is a capsule containing plural granules, beads, pellets, agglomerates, crystals, spheroids, microspheres, seeds, microcapsules, or mini-tablets.

4. The solid dosage form of claim 1, wherein the core contains one or more osmotic agents that promote a buildup of osmotic pressure in the core following contact with water.

5. The solid dosage form of claim 1, wherein the core further comprises one or more alkaline reacting compounds.

6. The solid dosage form of claim 1, wherein the core further comprises a disintegrant.

7. The solid dosage form of claim 1, wherein the time-release coating comprises one or more hydrophilic or hydrophobic polymers or additives that regulate the strength, erosion property and/or diffusion property of the coating.

8. The solid dosage form of claim 1, wherein the time-release coating comprises one or more of an electrolyte, clay, polysaccharide and a hydrophilic material that influences the period of time it takes for the external aqueous medium to reach the pellet or tablet core containing the drug.

9. The solid dosage form of claim 1, wherein the time-release coating begins to erode shortly after administration to a patient and continues to erode for a period of at least 1 hour after which it loses its physical integrity and exposes the core to the environment of use thereby providing a delayed release of omeprazole.

10. The solid dosage form of claim 1, wherein the time-release coating does not erode initially, but permits the diffusion of an aqueous fluid therein and delays exposure of the core to the aqueous fluid for a period of at least 1 hour after which time the core rapidly disintegrates and the time-release coating loses its physical integrity.

11. The solid dosage form of claim 1, wherein the time-release coating is about 100–5000 microns thick and delays the release of omeprazole from the core at least about 1 hour after administration.

12. The solid dosage form of claim 1, wherein the time-release coating delays the release of omeprazole from the core for a period of about 1–3.5 hours after administration.

13. The solid dosage form of claim 1, wherein the time-release coating further comprises one or more of a buffering agent, alkalizing agent, or combination thereof.

14. The solid dosage form of claim 1, wherein the time-release coating further comprises one or more of an erosion regulator or diffusion regulator.

15. The solid dosage form of claim 1, wherein the time-release coating is applied onto the core as a solution or suspension.

16. The solid dosage form of claim 1, wherein the time-release coating is compressed onto the core.

17. The solid dosage form of claim 1, wherein the time-release coating slowly dissolves or disintegrates in aqueous media having a pH in the range of about 1.2–8.0.

18. The solid dosage form of claim 1, wherein the alkalizing agent is selected from the group consisting of disodium hydrogen phosphate, dipotassium hydrogen phosphate, a phosphate salt, alkaline silicate, talc, kaolin, Veegum, bentonite, alkaline electrolyte, alkaline nonelectrolyte, amino acid, alanine, bicarbonate salt, carbonate salt, ammonia, ammonium carbonate, diethanolamine, monoethanolamine, potassium hydroxide, sodium borate, sodium carbonate, sodium bicarbonate, sodium hydroxide, triethanolamine, alkaline amino acid, organic amine base, and trolamine.

19. The solid dosage form of claim 1, wherein the core comprises an inert nonpareil seed, pellet, or tablet onto which at least omeprazole and an alkalizing agent are sprayed prior to application of the time-release coating.

20. The solid dosage form of claim 1, wherein the time-release coating comprises one or more components selected from the group consisting of HPMC, HPC, PVP, ethylcellulose, non-enteric acrylic polymer, protein, talc, clay, kaolin, glycerin monostearate, wax, silicon dioxide, polysaccharide, polyethylene oxide, and alkaline buffering agent.

21. The solid dosage form of claim 1, wherein the dosage form further comprises one or more additional non-enteric coatings.

22. The solid dosage form of claim 1, wherein the core comprises a tablet, pellet or agglomerate consisting of an inert substrate onto which is sprayed a dispersion comprising omeprazole, a pharmaceutical binder and an optional alkalizing agent.

23. The solid dosage form of claim 1, wherein the time-release coating further comprises an alkalizing agent, antioxidant, preservative or a combination thereof.

24. The solid dosage form of claim 1, wherein the osmotic agent swells when contacted by the aqueous fluid in the environment of use to aid in the disintegration of the time-release coating.

25. The solid dosage form of claim 2, wherein the granule, bead, pellet, tablet, agglomerate, crystal, spheroid, microsphere, seed, microcapsule, or mini-tablet is included in a compressed tablet core.

26. The solid dosage form of claim 1, wherein the time-release coating delays the release of omeprazole from the core for a period of about 1.5–2.5 hours after administration.

27. The solid dosage form of claim 1, wherein the time-release coating delays the release of omeprazole from the core for a period of about 0.5–5.0 hours after administration.

28. A solid dosage form that provides a delayed and subsequently rapid release of omeprazole into an environment of use, wherein the dosage form comprises:
   a core comprising omeprazole and at least one pharmaceutical excipient; and
   a time-release non-enteric water soluble or water erodible coating surrounding and in contact with the core, wherein the time-release coating comprises one or more of an erosion regulator or diffusion regulator that regulate the strength, erosion property and/or diffusion property of the coating; the coating delays the contact of the core with a fluid in an environment of use for a period of at least one-half hour to delay the release of the omeprazole from the core; and the coating subsequently loses its physical integrity in an essentially pH independent manner after the delay period thereby permitting the core to rapidly release the omeprazole into the environment of use; and
   wherein, the dosage form excludes an enteric release coating made from an enteric release polymer; the dosage form is adapted for oral administration; the time-release coating is sufficiently thick to retain its chemical and physical integrity in the stomach when administered orally; and the time-release coating loses its physical integrity in the upper portion of the GI tract downstream from the stomach of a subject to which the dosage form is administered.

29. The solid dosage form of claim 28, wherein the time-release coating delays the release of omeprazole from the core for a period of about 1–5.0 hours after administration.

30. The solid dosage form of claim 29, wherein the time-release coating is about 100–5000 microns thick.

31. The solid dosage form of claim 29, wherein the time-release coating slowly dissolves or disintegrates in aqueous media having a pH in the range of about 1.2–8.0.

32. The solid dosage form of claim 29, wherein the time-release coating further comprises one or more of a buffering agent, alkalizing agent, antioxidant, preservative or combination thereof.

33. The solid dosage form of claim 29, wherein the core further comprises one or more alkaline reacting compounds.

34. The solid dosage form of claim 29, wherein the core further comprises a disintegrant.

35. The solid dosage form of claim 28, wherein the time-release coating begins to erode shortly after administration to a patient and continues to erode for a period of at least 1 hour after which it loses its physical integrity and exposes the core to the environment of use thereby providing a delayed release of omeprazole.

36. The solid dosage form of claim 28, wherein the time-release coating does not erode initially, but permits the diffusion of an aqueous fluid therein and delays exposure of the core to the aqueous fluid for a period of at least 1 hour after which time the core rapidly disintegrates and the time-release coating loses its physical integrity.

37. The solid dosage form of claim 28, wherein the core comprises an inert nonpareil seed, pellet, or tablet Onto which at least omeprazole and an alkalizing agent are sprayed prior to application of the time-release coating.

38. The solid dosage form of claim 28, wherein the dosage form further comprises one or more additional non-enteric coatings.

39. The solid dosage form of claim 28, wherein the core comprises a tablet, pellet or agglomerate consisting of an inert substrate onto which is sprayed a dispersion comprising omeprazole, a pharmaceutical binder and an optional alkalizing agent.

40. A solid dosage form that provides a delayed and subsequently rapid release of omeprazole into an environment of use, wherein the dosage form comprises:

a core comprising omeprazole and at least one pharmaceutical excipient; and a time-release non-enteric water soluble or water erodible coating surrounding and in contact with the core, wherein the time-release coating comprises one or more of an erosion regulator or diffusion regulator that regulate the strength, erosion property and/or diffusion property of the coating; the time-release coating is about 100–5000 microns thick; and the time-release coating loses its physical integrity in an essentially pH independent manner and delays release of the omeprazole from the core into an environment of use for a period of at least 0.5–3.5 hours after exposure of the dosage form to the environment of use; and wherein, the dosage form excludes an enteric release coating made from an enteric release polymer; the dosage form is adapted for oral administration; the time-release coating is sufficiently thick to retain its chemical and physical integrity in the stomach when administered orally; and the time-release coating loses its physical integrity in the upper portion of the GI tract downstream from the stomach of a subject to which the dosage form is administered.

41. The solid dosage form of claim 40, wherein the time-release coating further comprises one or more of a buffering agent, alkalizing agent, antioxidant, preservative or combination thereof.

42. The solid dosage form of claim 40, wherein the time-release coating begins to erode shortly after administration to a patient and continues to erode for a period of at least 1 hour after which it loses its physical integrity and exposes the core to the environment of use thereby providing a delayed release of omeprazole.

43. The solid dosage form of claim 40, therein the time-release coating does not erode initially, but permits the diffusion of an aqueous fluid therein and delays exposure of the core to the aqueous fluid for a period of at least 1 hour after which time the core rapidly disintegrates and the time-release coating loses its physical integrity.

44. The solid dosage form of claim 40, wherein the core comprises an inert nonpareil seed, pellet, or tablet onto which at least omeprazole and an alkalizing agent are sprayed prior to application of the time-release coating.

45. The solid dosage form of claim 40, wherein the dosage form further comprises one or more additional non-enteric coatings.

46. The solid dosage form of claim 40, wherein the core further comprises one or more alkaline reacting compounds.

47. The solid dosage form of claim 40, wherein the core further comprises a disintegrant.

48. The solid dosage form is claim 40, wherein the core is a hard or soft capsule comprising a shell surrounding an omeprazole-containing composition, and the time-release coating surrounds the shell.

49. The solid dosage form is claim 1, wherein the core is a hard or soft capsule comprising a shell surrounding an omeprazole-containing composition, and the time-release coating surrounds the shell.

50. The solid dosage form is claim 28, wherein the core is a hard or soft capsule comprising a shell surrounding an omeprazole-containing composition, and the time-release coating surrounds the shell.

* * * * *